United States Patent [19]

Edwards

[11] 4,103,688
[45] Aug. 1, 1978

[54] METHOD AND APPARATUS FOR STERILIZATION

[76] Inventor: John Edwards, Rte. 1, County Rd. 550 S., Churubusco, Ind. 46723

[21] Appl. No.: 681,401

[22] Filed: Apr. 29, 1976

[51] Int. Cl.² ............................................. A61B 17/36
[52] U.S. Cl. .......................... 128/303.17; 128/303.18
[58] Field of Search ..................... 128/303.13, 303.14, 128/303.17, 303.18, 303.19, 405, 406, 407, 408

[56] References Cited

U.S. PATENT DOCUMENTS

| | | | |
|---|---|---|---|
| 2,102,270 | 12/1937 | Hyams | 128/408 X |
| 2,110,735 | 3/1938 | Marton | 128/303.18 |
| 2,700,975 | 2/1955 | Hopfinger et al. | 128/303.18 |
| 3,532,095 | 10/1970 | Miller | 128/303.13 |
| 3,645,265 | 2/1972 | Majzlin | 128/303.13 |
| 3,651,812 | 3/1972 | Samuels | 128/303.18 |
| 3,858,586 | 1/1975 | Lessen | 128/303.17 X |
| 4,034,762 | 7/1977 | Cosens et al. | 128/303.18 X |

FOREIGN PATENT DOCUMENTS

| | | | |
|---|---|---|---|
| 2,235,669 | 1/1975 | France | 128/408 |
| 651,428 | 9/1937 | Fed. Rep. of Germany | 128/303.17 |

OTHER PUBLICATIONS

Decker et al., "An Electrocautery Inst. . . . for Sterilization", Instrument Society of America, pp. 5-10, 1973.
Schmidt et al., "Vas Cautery; Battery Powered Inst. for Vasectomy", Urology, May 1974, vol. 3, No. 5, pp. 604-605.

Primary Examiner—Robert W. Michell
Assistant Examiner—Lee S. Cohen
Attorney, Agent, or Firm—Gust, Irish, Jeffers & Rickert

[57] ABSTRACT

A method and apparatus for sterilization wherein a flexible, non-resilient, filamentar electrode having an exposed cauterizing tip at one end thereof, and having a thin, dielectric, lubricous covering insulating the electrode up to the exposed tip, is inserted into a severed vas deferens. The electrode insertion is continued until the tip has been located a predetermined distance into the vas. This distance is less than the covering length so that the tip is contiguous with the inner vas walls but the remainder of the electrode is completely insulated therefrom. A second electrode is placed in electrical contact with the patient's body. A radio frequency (r.f.) energy source is applied to the other electrode end to cause r.f. energy flow from the tip to the inner vas wall. The tip is then withdrawn at a predetermined rate while applying r.f. energy to the electrode to thereby cauterize the inner walls which join together in permanent sperm-sealing relation.

8 Claims, 7 Drawing Figures

METHOD AND APPARATUS FOR STERILIZATION

BACKGROUND OF THE INVENTION

1. Field of the Invention

This invention is in the field of male sterilization wherein the vas deferens is sealed against sperm flow.

2. Brief Statement of the Prior Art

The male sterilization procedure, commonly known as vasectomy, has been performed for many years as a means of positive birth control. This procedure generally involves severing each of the vas deferens tubes in the scrotum and sealing the cut ends so that no sperm may be transmitted through the tubes past the sealed ends. Certain complications may arise as a result of vasectomies performed using procedures that are common and accepted by many surgeons. These procedures usually involve incising a section of each vas deferens and tying off the cut ends of the vas deferens with ligatures, which cause each vas end to heal to form a seal. Seals formed in this manner were in some cases unreliable.

Other prior art sterilization methods included inserting a wire in the vas, heating the wire causing cauterization of the vas walls and withdrawing the wire resulting in a sealing of the cauterized walls. This method suffered from the serious deficiency that the vas wall portions near the severed end were in continuous and prolonged contact with the heated wire, causing those portions to become overheated and burned. Chunks of the wall would adhere to the heated wire and thus weaken the wall structure, and necrosis of the outer tissues would occur causing sperm leakage which could lead to the situation that results in a recanalization of the divided vas with a resultant restoration of fertility, often unknown to the patient.

SUMMARY OF THE INVENTION

A vas deferens cauterizing instrument has a flexible, non-resilient, filamentar electrode with a cauterizing tip at one end. A conductor pin is secured to the other end of the electrode in electrical contact therewith. The pin is adapted to be removably received in electrical engagement by a socket assembly of an r.f. energy source. A thin, flexible non-resilient, lubricous dielectric electrode covering between the exposed tip and the pin forms electrode insulation.

In the method of this invention, the vas deferens is severed and the exposed tip is inserted a predetermined length therein. Once inserted, the tip is in contiguous relationship to the inner walls of the vas and the remainder of the electrode is completely insulated from the vas walls by the lubricous dielectric coating. A second electrode has been placed in electrical contact with the patient's body and the pin is plugged into an r.f. energy source. R.F. energy, is applied between the electrodes and, during continuous application of power to the electrode, the tip is slowly withdrawn from the vas. Due to the r.f. energy flow between the tip and the vas walls, a cauterizing action takes place, the cauterized walls joining to afterwards heal and form a permanent seal of the vas walls as the tip is withdrawn. Only the walls in contact with the tip are heated to cauterization temperature and therefore necrosis of the wall tissue, and adherence of wall tissue to electrode portions are prevented. The method is applied to both ends of both vas deferens in the scrotum. Due to the flexible non-resilient nature of the electrode and covering, the electrode is adaptable to access in confined areas greatly facilitating the use thereof. Thus, the vas walls are neither mutilated nor weakened by conventional sterilization methods.

It is therefore an object of this invention to provide a male sterilization method and apparatus that will provide a reliable seal of the vas deferens and minimize tissue damage to the vas and prevent seal failure.

It is a further object of this invention to provide a method and apparatus of the foregoing object that is usable in confined operating areas.

Another object of this invention is to provide in the method and apparatus of the foregoing objects a relatively inexpensive, disposable surgical instrument.

The above-mentioned and other features and objects of this invention and the manner of attaining them will become more apparent and the invention itself will be best understood by reference to the following description of an embodiment of the invention taken in conjunction with the accompanying drawings.

DESCRIPTION OF A PREFERRED EMBODIMENT

Figure 1:
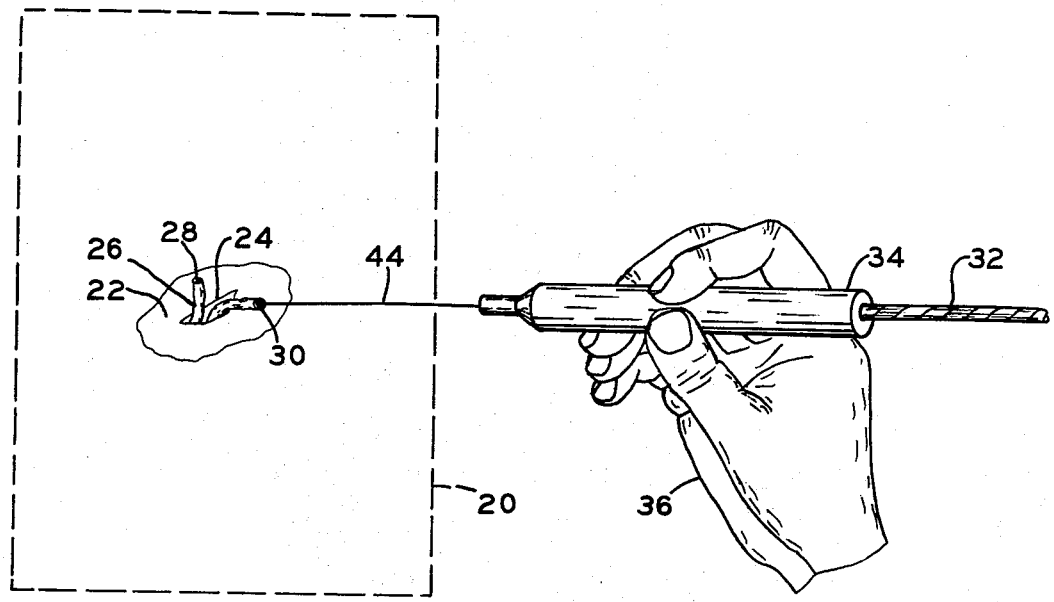
FIG. 1 is a partial, pictorial view of an embodiment of this invention, with a plate electrode shown in dashed lines, in operational relation to a vas deferens.

Referring to the drawing, in FIG. 1, a partial view of a patient's body, in electrical contact with a conductive plate 20 shown in dashed lines, includes a scrotum 22 having a surgically formed slit 24 therein with vas deferens, or sperm duct, 26 severed to form ends 28 and 30. A cable 32 from a conventional power supply, such as a Bovie power supply, not shown, for providing variable levels of radio frequency (r.f.) energy, is secured to an insulative handle 34 shown held in operating position by a surgeon's hand 36. The power supply is also electrically connected to plate 20, which may be of stainless steel. Handle 34 has a conductive sleeve 38 for receiving in electrically conductive relation pin 40. Pin 40 is secured in electrical conductive relation to electrode 42 as by solder joint 43. Electrode 42 in a working embodiment is preferably two inches long, and has a covering 44 of lubricous dielectric material, such as Teflon, completely insulating the length thereof to an exposed, rounded cauterizing tip 46. The length of tip 46 in a working embodiment in 0.3 centimeter or ⅛th inch. Electrode 42 in a working embodiment is 0.010 inches in diameter and formed of a 316 LV (soft) stainless steel material. Covering 44 may be one or more layers of Teflon and is relatively thin-walled and also covers a portion of pin 40. Pin 40 is removably secured in a friction fit within socket 38. Socket 38 receives a mating conductive member, not shown, from the power supply. Other methods of removably securing pin 40 in socket 38 may, of course, be employed.

Figure 2:
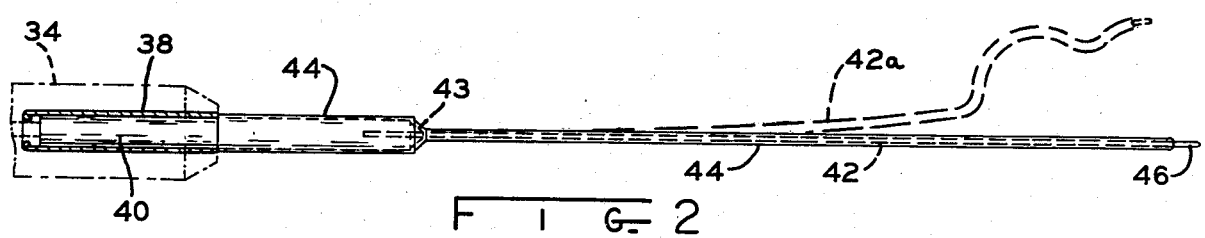
FIG. 2 is a plan view of an electrode of this embodiment with the electrode being shown in dashed lines in an alternative configuration.
Figure 3:
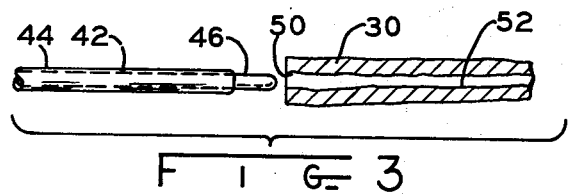
FIG. 3 is a partial view of an apparatus of this invention prior to insertion in a vas deferens.

Electrode 42 with covering 44 is flexible, pliable, and non-resilient so that it may be retentively configured by the surgeon in any required shape, as shown at 42a in FIG. 2, to facilitate its use in confined quarters and also to conform to the nonlinearities of a vas deferens.

Figure 4:
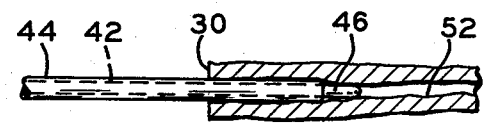
FIG. 4 is a view similar to FIG. 3 after the device has been inserted into the vas deferens.
Figure 5:
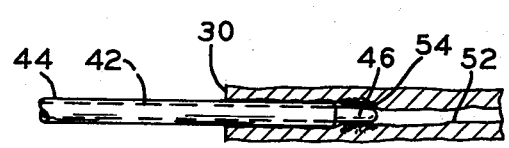
FIG. 5 is a view similar to FIG. 4 after the power has been applied to the device electrode.

In the method of this invention, the surgeon first opens scrotum 22 to form slit 24, withdraws a portion of the vas, makes two ligations spaced apart, and removes a one inch length therebetween leaving end portions of vas deferens exposing ends 28 and 30. Insulated electrode 42 is then aligned for insertion of exposed tip 46 in tubular opening or mouth 50 of vas 30. Tip 46 is then inserted into opening 50 to a distance of preferably not less than approximately 1.3 centimeters, or $\frac{1}{2}$ inch, to the position of FIG. 4. The inner walls 52 of vas 30 are contiguous with tip 46 and insulative layer 44. At this point the surgeon applies r.f. energy, preferably less than 250 watts, as with a foot switch or the like, not shown, to electrode 42. This causes cauterization 54, FIG. 5, of walls 52 due to the r.f. energy flow from tip 46 through the patient to electrode plate 20.

Figure 6:
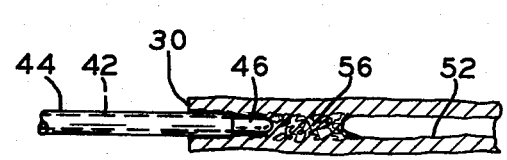
FIG. 6 is a view similar to FIG. 5 during withdrawal of the electrode tip from the vas deferens.
Figure 7:
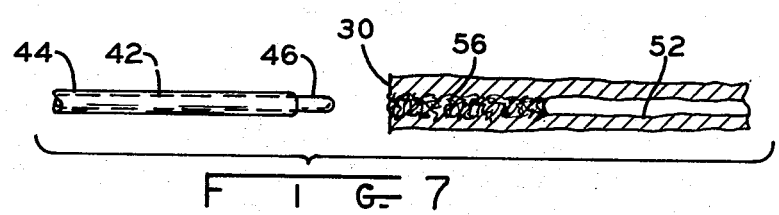
FIG. 7 is a view similar to FIG. 6 wherein the electrode tip has been withdrawn from the vas showing the cauterized seal.

Simultaneously, the surgeon begins a slow withdrawal of electrode 42 from vas 30 with the freshly cauterized portions 54 of wall 52 joining to form a permanent seal 56, FIG. 6, in duct 30. The withdrawal of electrode 42 is continued, while applying the r.f. energy thereto, until the electrode is completely withdrawn, FIG. 7, completely sealing duct end 30. End 28 is similarly sealed and the other vas deferens is cut, and the ends thereof are also sealed in similar fashion to seal exit of sperm and its carrier fluid from the testis and entrance of the duct leading to the seminal vesicles.

Thus, only an increment of the vas walls 52 located at a predetermined distance inwardly of orifice 50 is initially cauterized. Then, subsequent increments in a continuous sequence from the initial increment to the vas orifice 50 are cauterized and sealed. No increment is subjected to prolonged, continuous heating that would cause over-burning and necrosis of the vas and adjacent flesh, and adherence of vas wall portions to the electrode 42. Thus, severe weakening of the vas walls is prevented. If the withdrawal rate of tip 46 is uniform, all vas increments will be uniformly heated for uniform periods.

It is to be understood that in actual practice, the surgeon would grasp a portion of the electrode 42/44 with one hand and the vas end 30 with the other hand and thread the tip 46 into the vas the proper distance. Also, it is to be understood that the vas deferens may be obtained through other portions of the body than the scrotum.

While there have been described above the principles of this invention in connection with specific apparatus, it is to be clearly understood that this description is made only by way of example and not as a limitation to the scope of the invention.

What is claimed is:

1. A vas deferens cauterizing instrument for use with an energy source comprising:
   a flexible, non-resilient, pliable, filamentar elongate electrode of a size to be slidably inserted within a vas deferens and capable of being retentively configured to conform to the shape of the vas deferens having an exposed cauterizing tip of predetermined length at one end;
   a conductive connecting member secured to the other end of said electrode and in electrical contact therewith, and adapted to be removably received in electrical engagement with the energy source;
   a thin, flexible, lubricous, dielectric covering on said electrode along its length from said member to said exposed cauterizing tip for low friction sliding engagement with the inner walls of the vas deferens; and
   said cauterizing tip being electrically exposed to transmit energy directly to the inner walls of said vas deferens to cause cauterization and resultant sealing thereof on withdrawal of the tip from the vas deferens.

2. The device of claim 1 wherein said electrode extends approximately 2 inches from said member; and said electrically exposed tip is approximately $\frac{1}{8}$ inch long.

3. The device of claim 1 wherein said electrode is approximately 0.010 inch in diameter and is 316 LV stainless steel.

4. A method of sealing a vas deferens for patient sterilization comprising the steps of:
   severing a vas to provide severed vas ends;
   inserting into a vas end a flexible, non-resilient, pliable, filamentar electrode having a dielectric, lubricous coating and an exposed cauterizing tip at one end, the electrode capable of being retentively configured to conform to the shape of the vas.
   continuing electrode insertion until the tip is inserted a predetermined distance into the vas, whereby the tip is contiguous with the inner vas walls and the remainder of the electrode is insulated from the inner vas walls;
   placing a second electrode in electrical contact with the patient's body;
   applying an r.f. energy source between the electrodes to cause an r.f. energy flow from the tip to the inner vas walls to cauterize the inner vas walls; and
   withdrawing said tip at a predetermined rate while continuing said next previous step to thereby cauterize and adhere the inner walls in permanent sperm sealing relation.

5. The device of claim 4 wherein said step of applying an r.f. energy source comprises applying less than 250 watts of r.f. energy between said electrodes.

6. The device of claim 4 wherein the step of severing the vas comprises removing approximately one inch of the vas.

7. A method of sealing the vas deferens for patient sterilization comprising the steps of:
   severing a vas to provide severed vas ends;
   cauterizing only an increment of the inner walls of the vas at a section located a predetermined length from a vas end; and
   cauterizing increments of the inner walls of the vas in a continuing sequence along said entire predetermined length from said section towards said vas end, whereby the cauterized increments will join in a sperm seal.

8. The device of claim 7 wherein the step of cauterizing the inner walls is begun at a section at least $\frac{1}{2}$ inch from the vas end.

* * * * *